United States Patent
Yagyu et al.

(10) Patent No.: US 8,123,024 B2
(45) Date of Patent: Feb. 28, 2012

(54) VIBRATING FEEDER, CARRYING DEVICE AND INSPECTION DEVICE

(75) Inventors: Motohiro Yagyu, Yamatokoriyama (JP);
Kenichi Kasai, Yamatokoriyama (JP);
Ken Sato, Yamatokoriyama (JP);
Junsuke Yasui, Yamatokoriyama (JP);
Akira Nagao, Yamatokoriyama (JP);
Tetsuhisa Ishida, Yamatokoriyama (JP)

(73) Assignee: Qualicaps Co., Ltd., Nara (JP)

( * ) Notice: Subject to any disclaimer, the term of this patent is extended or adjusted under 35 U.S.C. 154(b) by 331 days.

(21) Appl. No.: 12/602,304

(22) PCT Filed: Apr. 25, 2008

(86) PCT No.: PCT/JP2008/058120
§ 371 (c)(1),
(2), (4) Date: Nov. 30, 2009

(87) PCT Pub. No.: WO2008/155950
PCT Pub. Date: Dec. 24, 2008

(65) Prior Publication Data
US 2010/0175968 A1 Jul. 15, 2010

(30) Foreign Application Priority Data
Jun. 19, 2007 (JP) ................................. 2007-161643

(51) Int. Cl.
*B65G 47/14* (2006.01)
(52) U.S. Cl. .......................... 198/757; 198/759; 198/771
(58) Field of Classification Search .................. 198/757, 198/759, 771
See application file for complete search history.

(56) References Cited

U.S. PATENT DOCUMENTS

| | | | | |
|---|---|---|---|---|
| 2,973,548 A * | 3/1961 | Walker | .......................... | 198/392 |
| 3,125,208 A * | 3/1964 | Secunda | ....................... | 198/391 |
| 3,655,032 A * | 4/1972 | Willis | ........................... | 198/757 |
| 4,563,268 A * | 1/1986 | Smith | ........................... | 209/257 |
| 5,044,487 A | 9/1991 | Spatafora et al. | | |

(Continued)

FOREIGN PATENT DOCUMENTS
JP 60-40325 3/1985
(Continued)

OTHER PUBLICATIONS

International Search Report issued Jul. 1, 2008 in International (PCT) Application No. PCT/JP2008/058120.

*Primary Examiner* — Mark A Deuble
(74) *Attorney, Agent, or Firm* — Wenderoth, Lind & Ponack, L.L.P.

(57) ABSTRACT

A vibrating feeder provided with a feeder ball 14a having a circular bottom wall and a conveyance path formed along the periphery of the bottom wall 141a; a feeder body 16a supporting the feeder ball 14a so as to apply torsional vibration and conveying substance supplied on the bottom wall 141a along the conveyance path; and a main body supporting member for supporting the feeder body; the conveyance path comprising an ascending rail and descending rail disposed in the downstream of the ascending rail in the conveyance direction; the main body 18a supporting member supporting the feeder body 16a on a horizontal floor so that a torsion axis C, which becomes the center of the torsional vibration, is inclined relative to the vertical direction; the ascending rail and descending rail conveying the conveyed objects upwardly or downwardly relative to the horizontal direction while the feeder body being supported by the horizontal floor via the main body supporting member.

10 Claims, 15 Drawing Sheets

U.S. PATENT DOCUMENTS

| | | | |
|---|---|---|---|
| 5,804,772 A * | 9/1998 | Wooldridge et al. | 177/116 |
| 7,036,652 B2 * | 5/2006 | Hayata et al. | 198/391 |
| 2006/0201788 A1 * | 9/2006 | Narukawa et al. | 198/757 |

FOREIGN PATENT DOCUMENTS

| | | | |
|---|---|---|---|
| JP | 62157117 A * | 7/1987 | 198/757 |
| JP | 2-305708 | 12/1990 | |
| JP | 3-102009 | 4/1991 | |
| JP | 6-115667 | 4/1994 | |
| JP | 6-255756 | 9/1994 | |
| JP | 6-286861 | 10/1994 | |
| JP | 2000-309421 | 11/2000 | |
| JP | 2001-33392 | 2/2001 | |
| JP | 2007-76819 | 3/2007 | |

* cited by examiner

[Fig. 1]
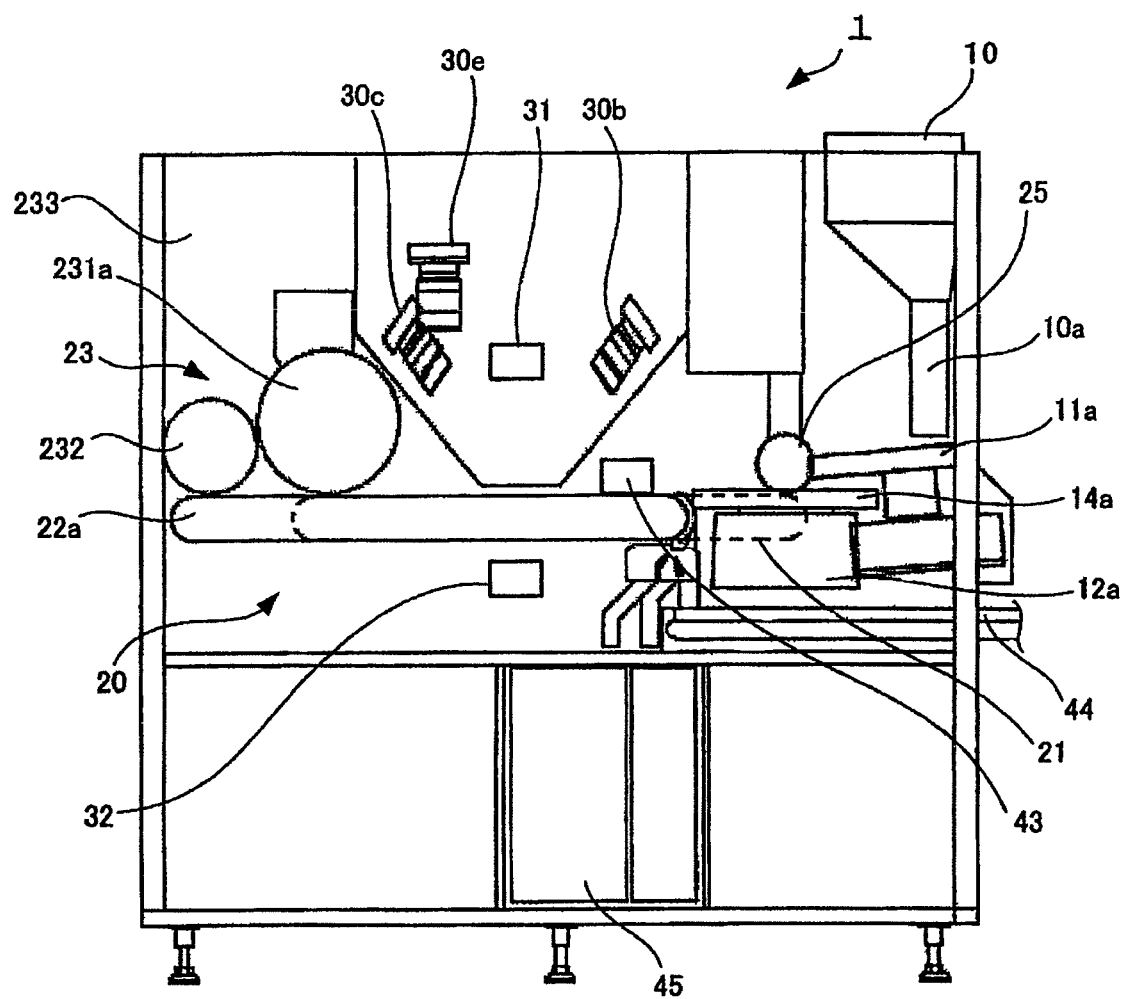

[Fig. 2]
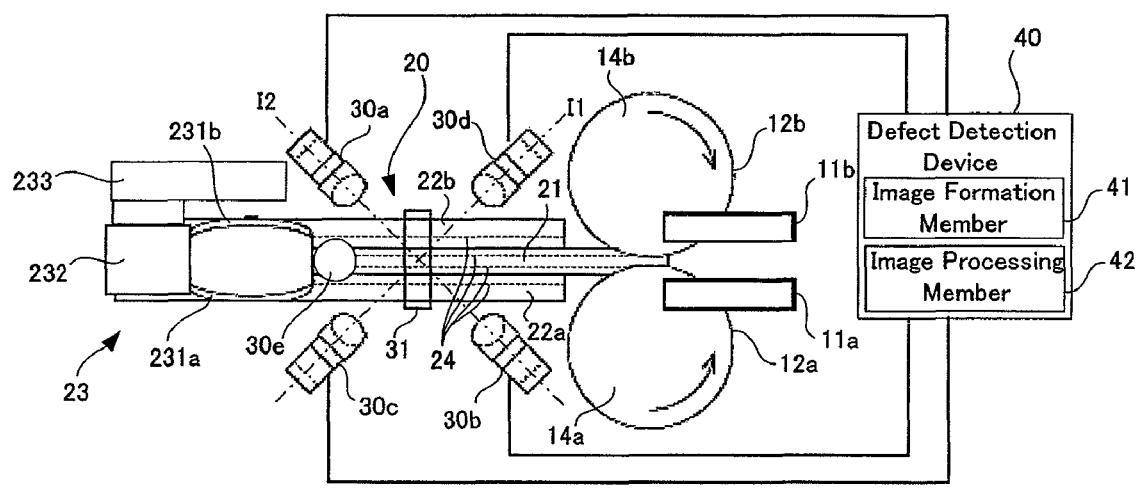

[Fig. 3]
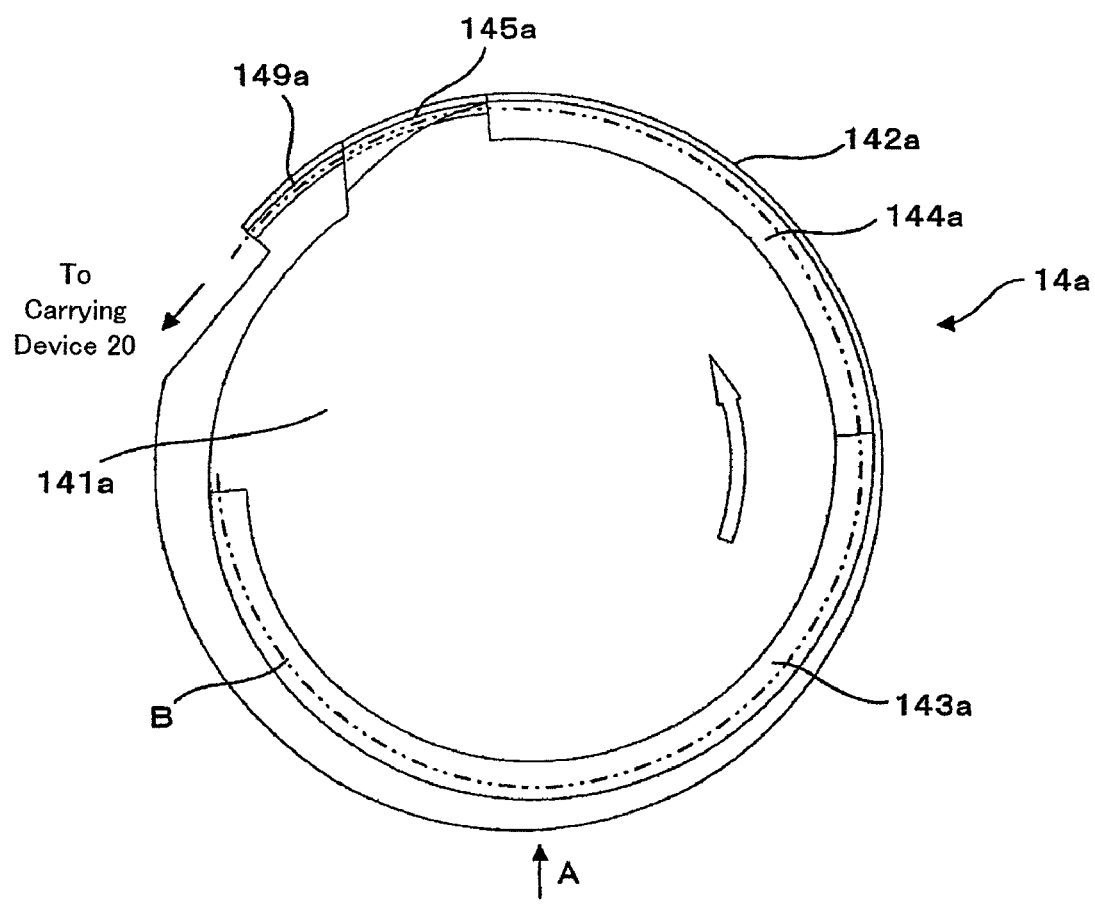

[Fig. 4]
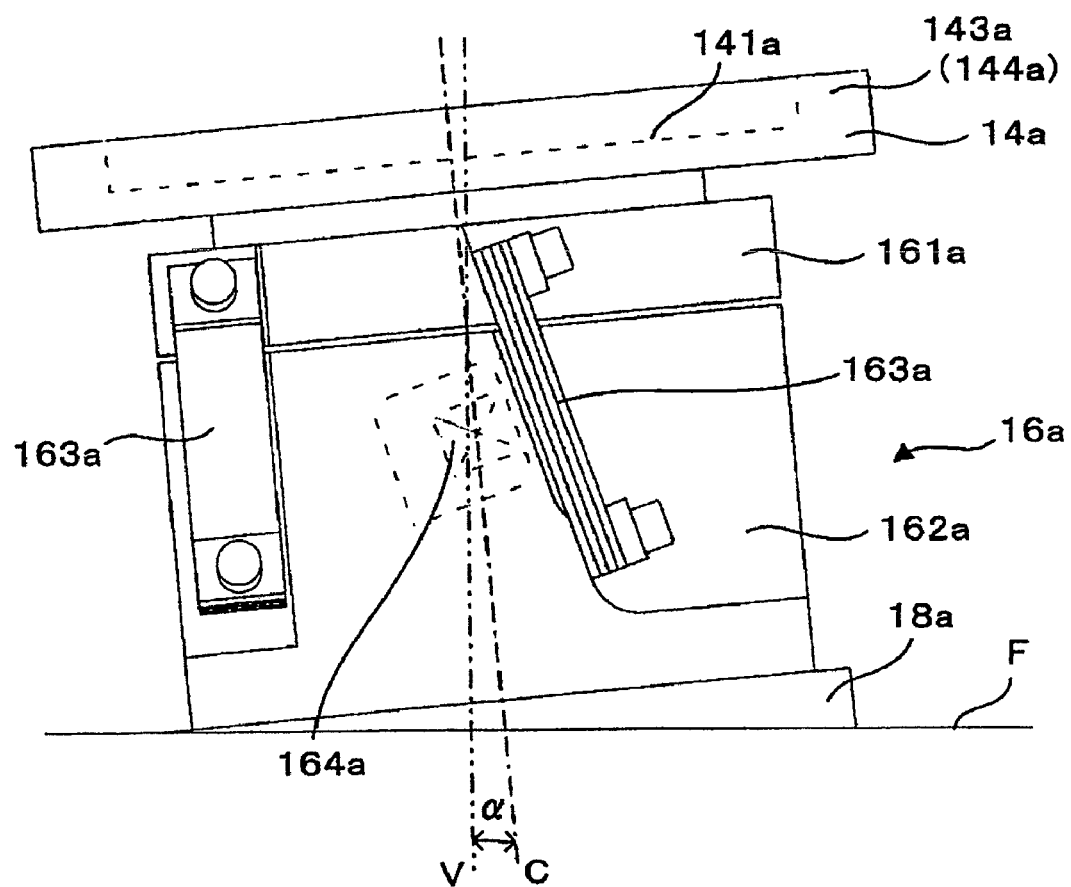

[Fig. 5]
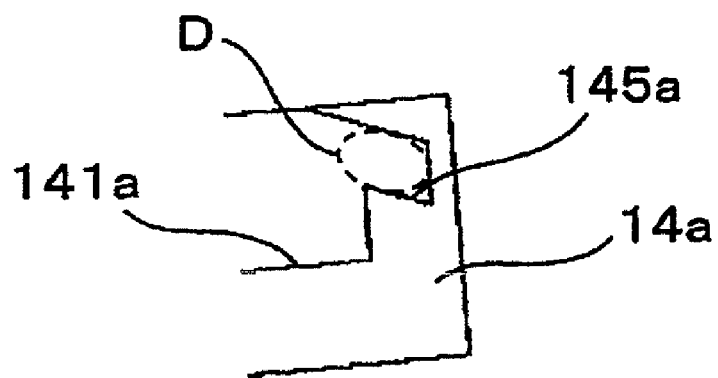

[Fig. 6]
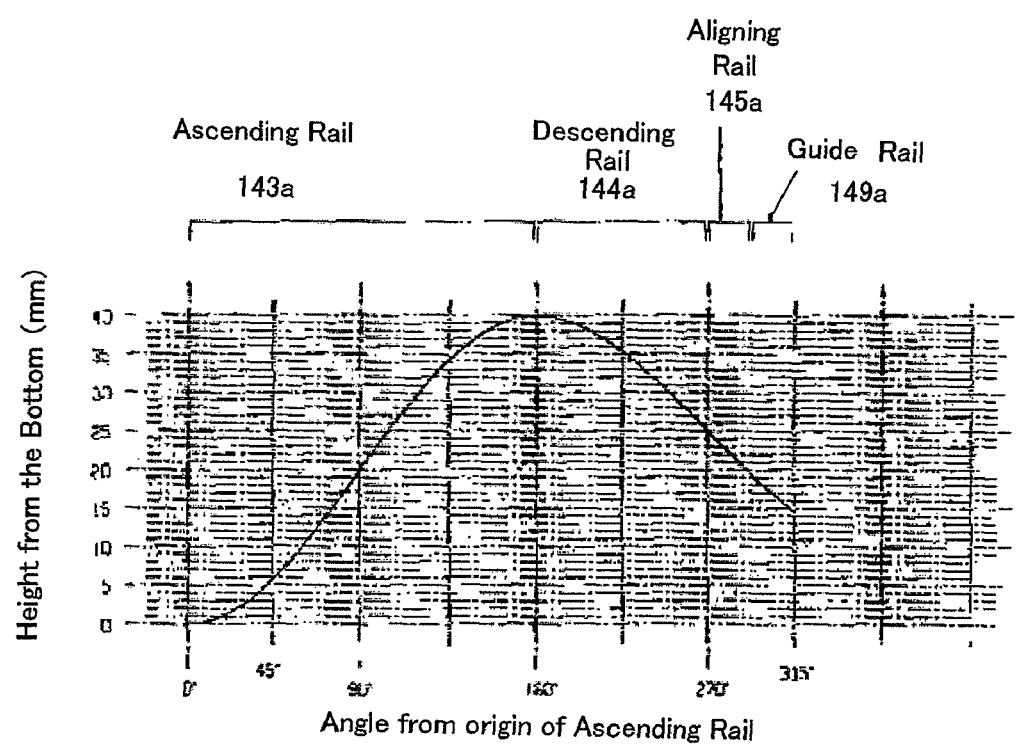

[Fig. 7]
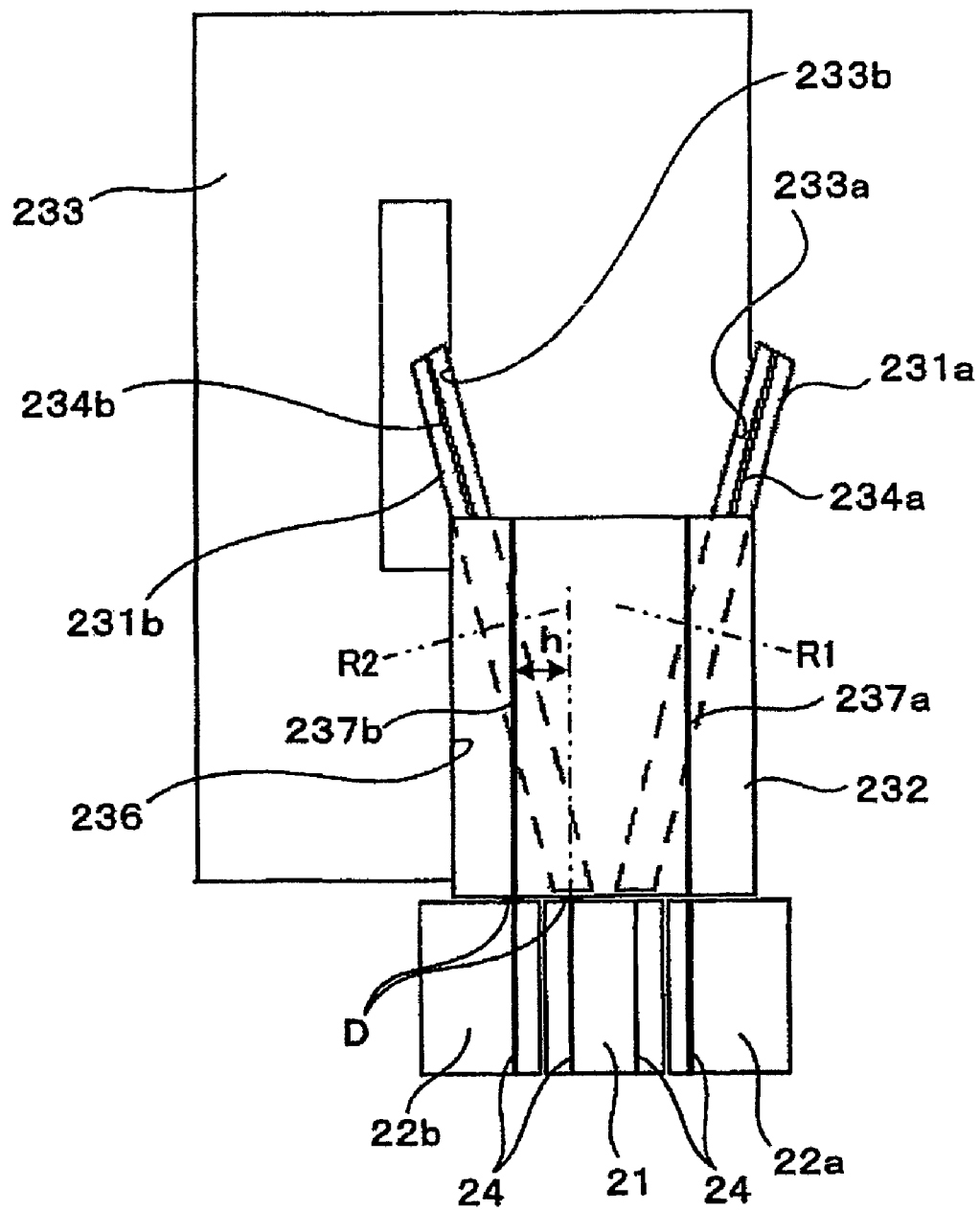

[Fig. 8]
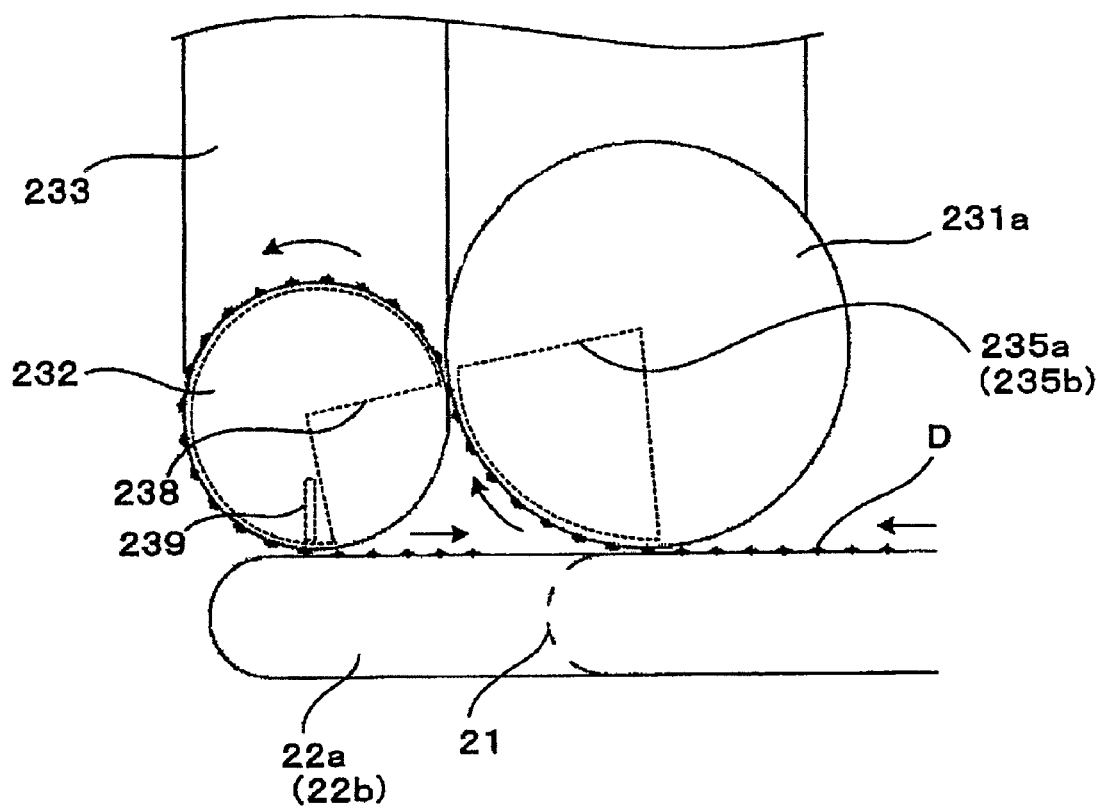

[Fig. 9]
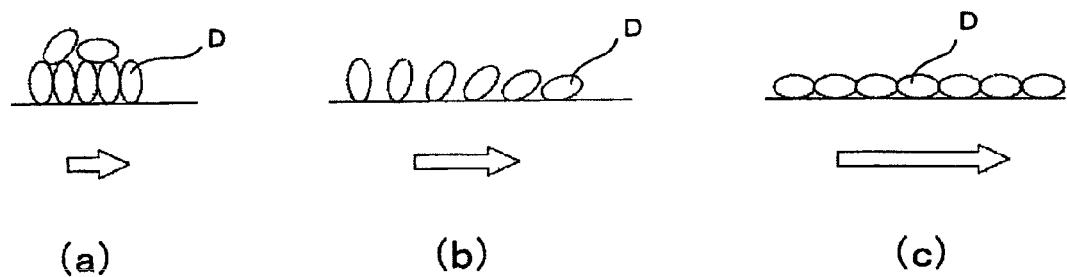
(a)  (b)  (c)
[Fig. 10]
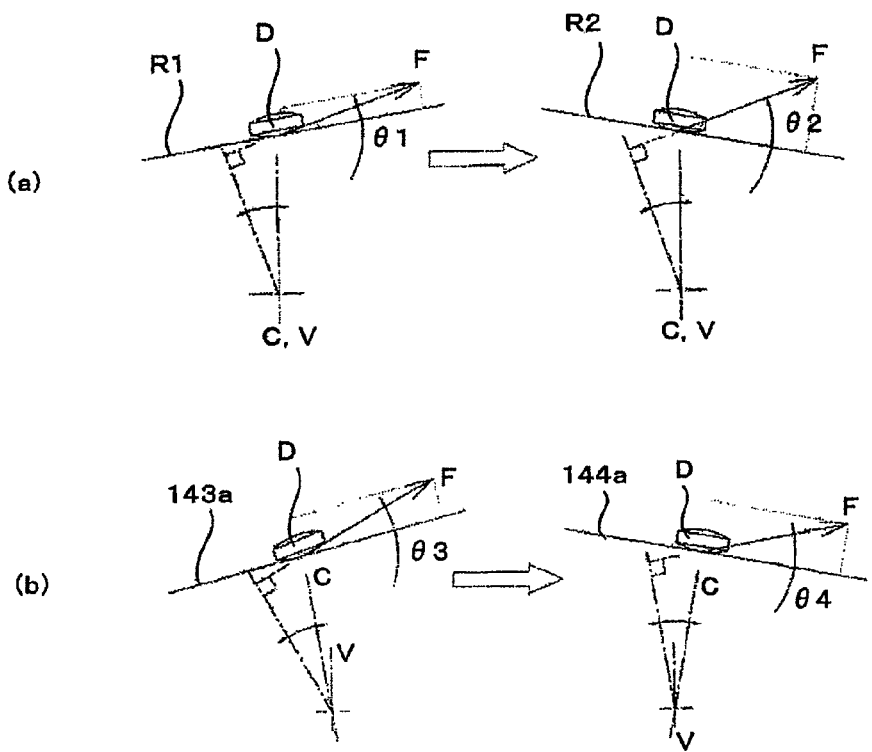
(a)
(b)

[Fig. 11]
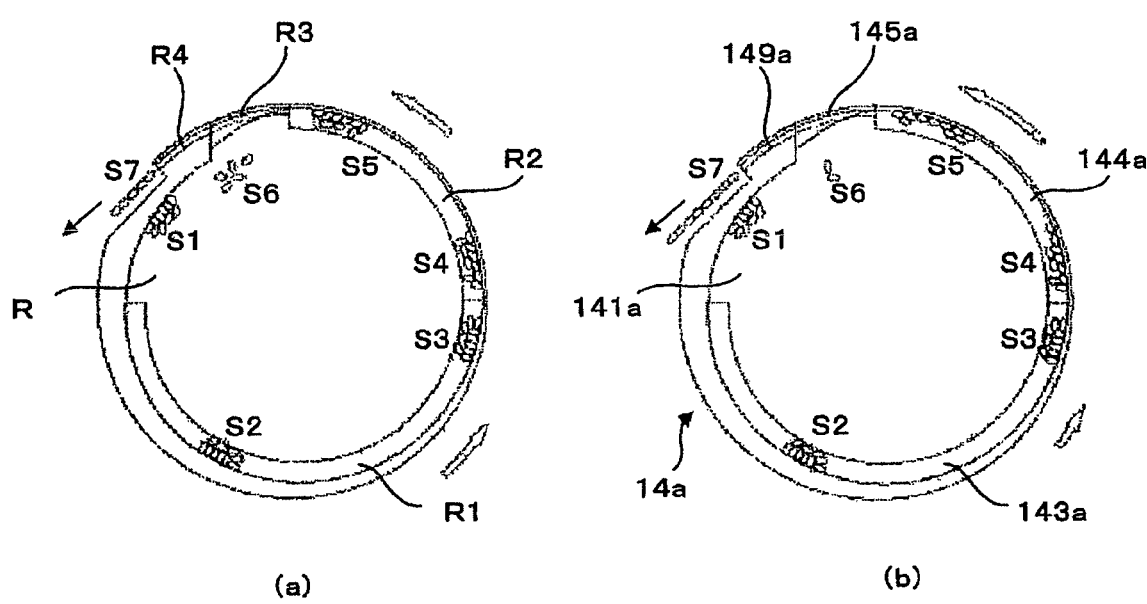

[Fig. 12]
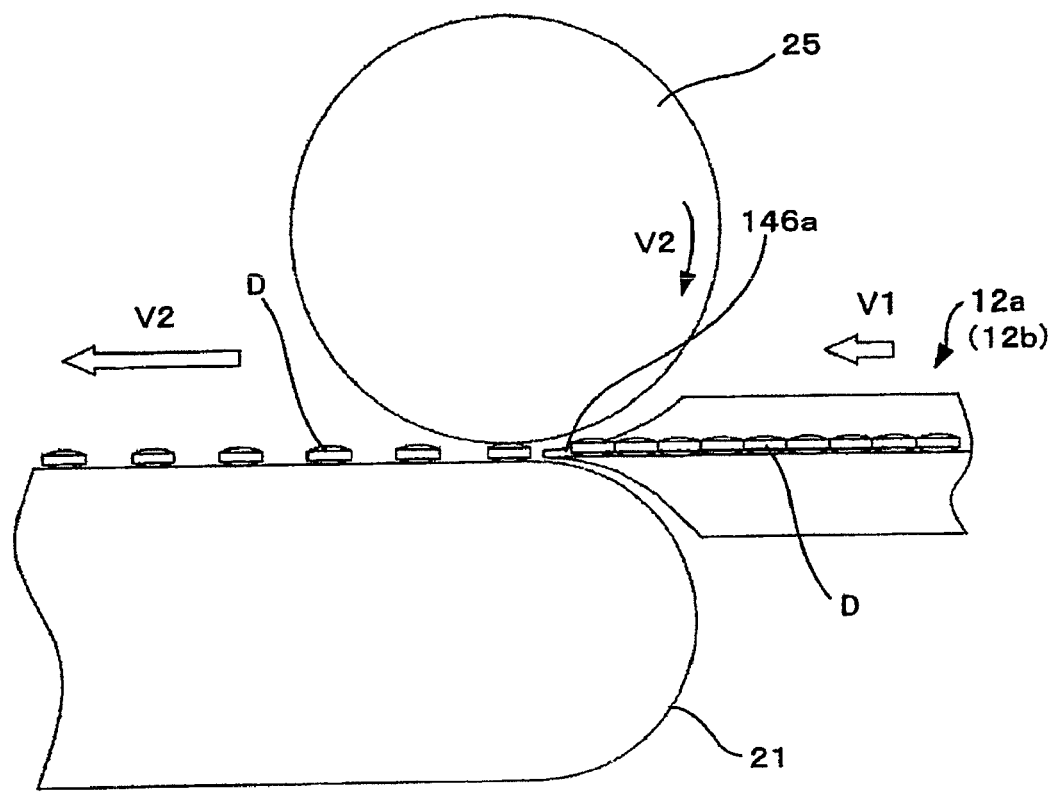

[Fig. 13]
(a)
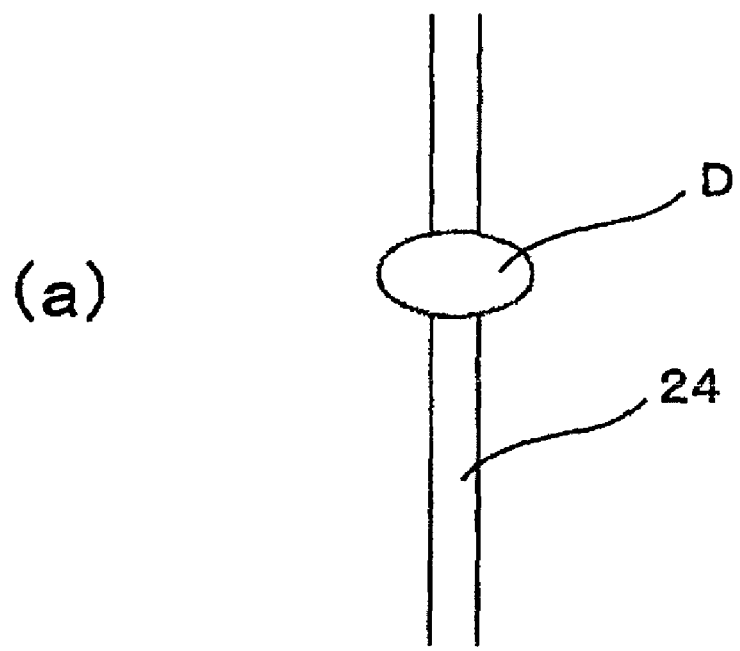
(b)
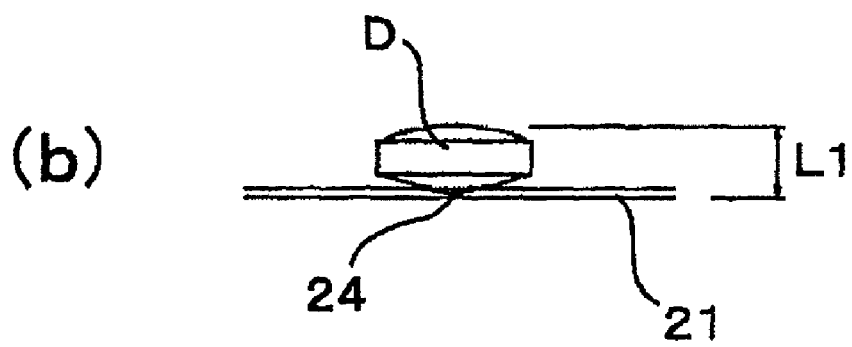

[Fig. 14]
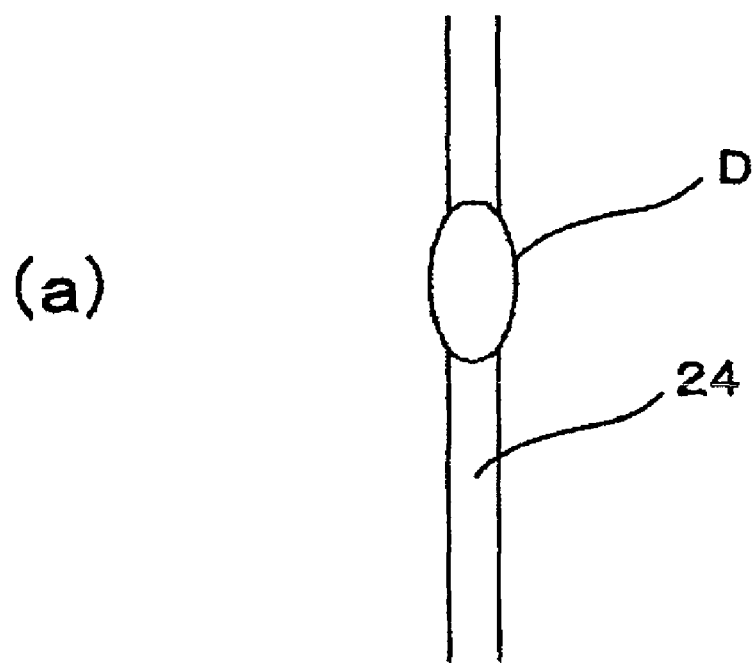
(a)
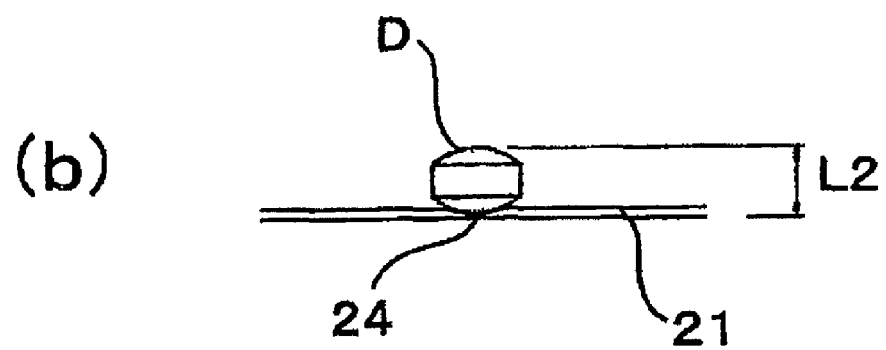
(b)

[Fig. 15]
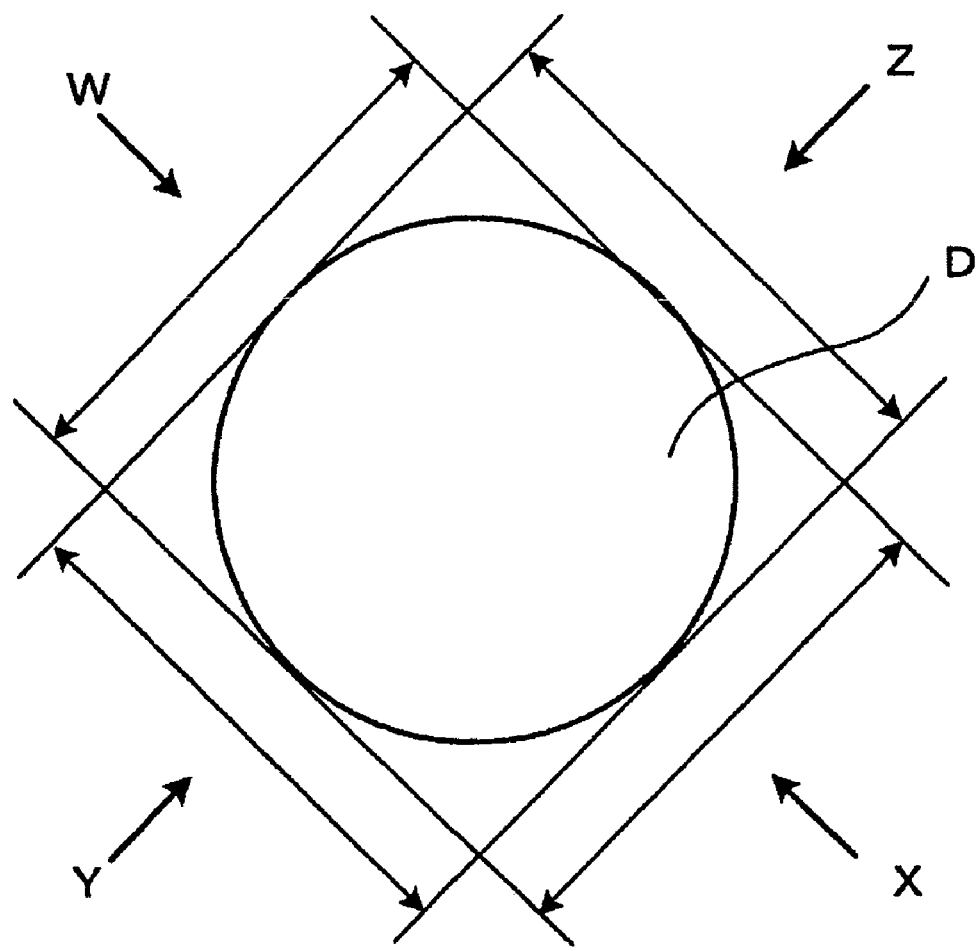

[Fig. 16]
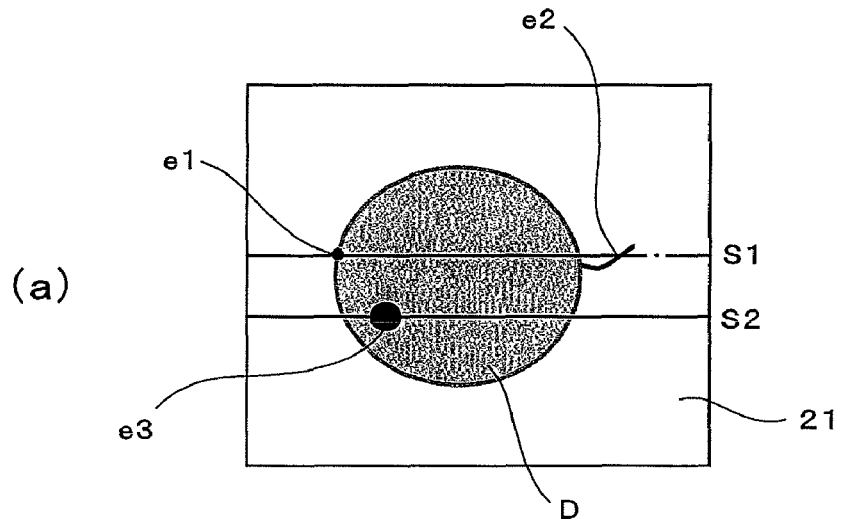
(a)
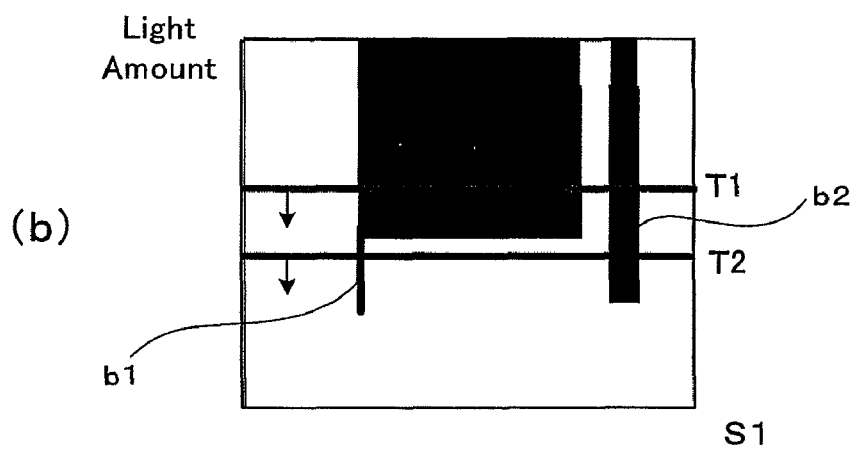
(b)
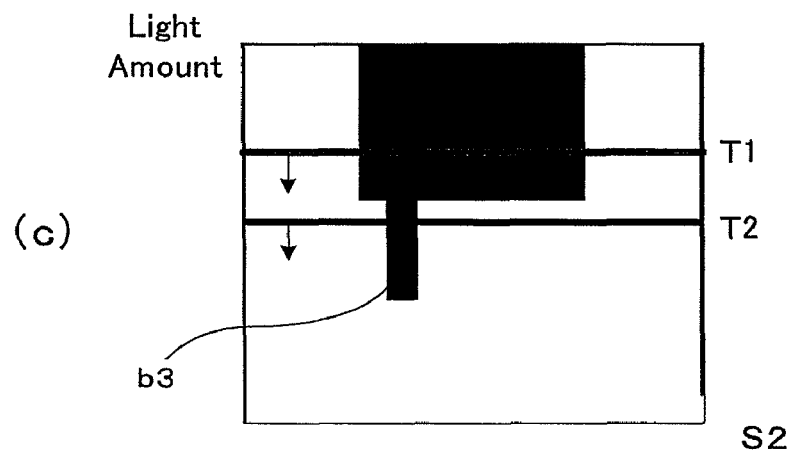
(c)

VIBRATING FEEDER, CARRYING DEVICE AND INSPECTION DEVICE

TECHNICAL FIELD

The present invention relates to a vibrating feeder for carrying tablets, capsules and like objects by vibration. Furthermore, the present invention relates to a carrying device and inspection device provided with such vibrating feeder.

BACKGROUND ART

There are several conventionally known devices for use in inspecting the appearance of tablets or like conveyed objects while transporting them, so that adhesion of foreign matter, contamination, cracking of the conveyed objects and like defects can be detected. For example, Patent Document 1 discloses an appearance inspection device by which tested objects placed in a hopper are supplied to a vibrating feeder, and then the objects are conveyed with vibration in an aligned state by the vibrating feeder. The tested objects are supplied from the vibrating feeder to an inspection drum where the appearance inspection is conducted.

Tested objects are continuously supplied from the hopper to the feeder ball, which forms the conveyance plane of the vibrating feeder. Therefore, the tested objects are conveyed in a condition such that they are piled onto the feeder ball, and this may hinder the constant feeding of the tested objects. To prevent this, Patent Document 2 discloses a structure wherein the excessive supply of the tested objects is prevented by providing a leveling plate in a conveyance path so that the height of the pile of tested objects is leveled.

Patent Document 1: Japanese Unexamined Patent Publication No. 2001-33392

Patent Document 2: Japanese Unexamined Patent Publication No. 2007-76819

DISCLOSURE OF THE INVENTION

Problem to be Solved by the Invention

The vibrating feeder disclosed in Patent Document 2 forcibly controls the conveyance amount of the objects by providing a leveling plate so as to narrow the space through which the objects pass. Therefore, the tested objects may easily crack or break when they pass through the leveling plate due to the impact or external force applied thereto. In recent years, in order to enhance inspection efficiency, vibrating feeders having a very high conveyance speed are demanded, and therefore the above described problem has become more critical than ever.

An object of the present invention is to provide a vibrating feeder that can align and convey objects at a high conveyance speed without damaging them. Another object of the present invention is to provide a carrying device and inspection device provided with such a vibrating feeder.

Means for Solving the Problem

An object of the present invention can be achieved by a vibrating feeder that is provided with a feeder ball having a circular bottom wall and a conveyance path formed along the periphery of the bottom wall; a feeder body for supporting the feeder ball so as to apply torsional vibration and for conveying objects supplied to the bottom wall along the conveyance path; and a main body supporting member for supporting the feeder body.

In the vibrating feeder, the conveyance path has an ascending rail and a descending rail that is disposed downstream from the ascending rail in the conveyance direction.

The main body supporting member supports the feeder body on a horizontal floor so that a torsion axis, which is the center of the torsional vibration, is inclined relative to the vertical direction.

The ascending rail and the descending rail respectively convey objects upwardly or downwardly relative to the horizontal direction with the feeder body being supported by the horizontal floor via the main body supporting member.

An object of the present invention can also be achieved by a carrying device provided with the above-described vibrating feeder for use in conveying objects, having a conveying means for receiving the objects delivered by the vibrating feeder and conveying the objects in a single direction; and press rollers for pressing the objects against the conveyance plane of the conveying means disposed in the location where the objects are transferred from the vibrating feeder to the conveying means.

An object of the present invention can also be achieved by an appearance inspection device provided with the above-described vibrating feeder for inspecting the appearance of the objects, having a forward conveying means for receiving the objects delivered by the vibrating feeder and conveying the objects in a single direction; a returning means for conveying the objects in the direction opposite to that of the forward conveying means, the returning means being disposed in parallel to the forward conveying means; and a back/front reversal means for turning over the front and back surfaces of the objects delivered by the forward conveying means and supplying the objects to the returning means; a plurality of image-pickup means for capturing images of each object from upper oblique directions along the same scanning line while the object is being conveyed by the forward conveying means and returning means; and a defect detection means for detecting the presence of defects based on image data captured by the image-pickup means.

Effect of the Invention

The vibrating feeder, carrying device and inspection device of the present invention make it possible to convey objects in an aligned condition at a high speed without damaging the objects.

BEST MODE FOR CARRYING OUT THE INVENTION

Hereunder, an embodiment of the present invention is explained in detail with reference to the attached drawings. FIG. 1 shows a side elevation view of the appearance inspection device according to one embodiment of the present invention, and FIG. 2 is a plan view of the main components of the appearance inspection device of FIG. 1.

As shown in FIGS. 1 and 2, the appearance inspection device 1 is provided with a hopper 10 through which tablets and like conveyance objects are supplied; vibrating feeders 12a and 12b for conveying the objects supplied from the hopper 10 while aligning them; a carrying device 20 for conveying the objects sequentially supplied from the vibrating feeders 12a and 12b; five image-pickup devices 30a, 30b, 30c, 30d and 30e for capturing images of the objects being conveyed by the carrying device 20; and a defect detection device 40 for detecting the existence of defects in the objects based on image data of each of the image-pickup devices 30a to 30e.

The vibrating feeders 12a and 12b are adjacently provided on the right and left of the hopper 10. The conveyed objects are supplied from the two outlets 10a and 10b formed in the lower portion of the hopper 10 via chutes 11a and 11b respectively. The objects supplied to the vibrating feeders 12a and 12b are conveyed by vibration in the direction shown by the arrow in FIG. 2.

FIG. 3 shows an enlarged plan view of a feeder ball 14a that serves as a conveyance plane of the vibrating feeder 12a. The feeder ball 14a has a circular bottom wall 141a and an annular guide wall 142a provided along the rim of the bottom wall 141a. At the periphery of the bottom wall 141a, an ascending rail 143a, descending rail 144a, and aligning rails 145a are disposed in such a manner that they sequentially connect in this order along the guide wall 142a.

FIG. 4 is a side elevation view of one of the vibrating feeders 12a, which is seen from the direction of arrow A in FIG. 3. The vibrating feeder 12a is provided with the above-described feeder ball 14a, a feeder body 16a for supporting the feeder ball 14a, and a main body supporting member 18a for supporting the feeder body 16a.

The feeder body 16a is provided with a vibration body 161a to which a feeder ball 14a is attached and a base 162a disposed below the vibration body 161a. Both of the vibration body 161a and base 162a have a cylinder-like shape and are connected to each other by a plurality of plate springs 163a that are disposed along the circumferential direction with regular intervals therebetween. Each of the plate springs 163a has a specific inclination relative to the central line C direction of the vibration body 161a and base 162a.

The base 162a is provided with an electromagnet 164a in a concave portion in the central portion thereof, and by causing the movable core (not shown) attached to the vibration body 161a to face the pole surface of the electromagnet 164a, torsional vibration can be applied to the vibration body 161a. The torsion axis, which functions as the center of the torsional vibration, is aligned with the central line C of the feeder ball 14a, vibration body 161a and base 162a. The structure for applying torsional vibration to the vibration body 161a is not limited to that of the present embodiment, and a known structure can be selected, for example, a plate spring is driven by supplying a voltage using a piezoelectric element.

The main body supporting member 18a is attached to the bottom surface of the cylindrical base 162a with a vibration isolator (not shown) formed from rubber or spring therebetween. The main body supporting member 18a is formed to have a wedge-like shape as seen from the side view, and supports the feeder body 16a on the horizontal floor surface F in such a manner that the central line C of the vibration body 161a and the base 162a is inclined relative to the vertical direction V. The main body supporting member 18a may be structured so as to be fixable to the floor surface F using a bolt or like connecting member. The feeder body 16a and the main body supporting member 18a do not have to be separately formed, and the main body supporting member 18a may be integrally formed in the lower portion of the feeder body 16. In this case, the main body supporting member 18a may be structured so as to be fixed to a supporting plate (not shown) or like horizontal floor via a vibration isolator. If the angle α formed between the vertical direction V and the central line C is unduly small, achieving the effects of the present invention tends to become difficult, and when the angle α is unduly large, conveyance of the objects tends to become difficult. The angle α can be suitably selected considering these facts. According to the experimental results described later, the angle α is preferably in the range of 1° to 10°, more preferably 2° to 7°, and even more preferably 3° to 7°. However, as long as a vibrating feeder 12a having a satisfactorily high conveyance ability is usable, the angle α may be greater than 10°.

As shown by the dashed line in FIG. 4, the conveyance planes of the ascending rail 143a and the descending rail 144a are downwardly inclined toward the outer radial direction when the vibrating feeder 12a is disposed on the horizontal floor surface F. This structure makes it easier to convey the objects on the ascending rail 143a and descending rail 144a along the guide wall 142a, facilitating aligned conveyance. The aligning rail 145a disposed downstream from the descending rail 144a in the conveyance direction has a narrower conveyance path as shown in FIG. 5 so as to hold a single line of the objects D, and excessive objects D that are not introduced into the guide rail 145a fall on the bottom wall 141a. As far as the objects can be conveyed in an aligned condition, the aligning rail 145a may be formed so as to have a plurality of conveyance lines. The objects that have passed through the aligning rail 145a are kept in an aligned condition as shown in FIG. 3 by the guide rail 149a and are then supplied to the carrying device 20. The guide rail 149a is not necessarily required and the objects may be supplied directly to the carrying device 20 from the end of the aligning rail 145a.

FIG. 6 is a side elevation view illustrating the inclination condition of the ascending rail 143a, the descending rail 144a, the aligning rail 145a, and the guide rail 149a of FIG. 3 as developed along the chain double-dashed line B, which is the conveyance direction as seen in a plan view. The inclination condition of FIG. 6 corresponds to the case where the angle α made between the vertical direction V and the central line C shown in FIG. 4 is 5°. In other words, the graph of FIG. 6 illustrates the relationship between the angle relative to the center of the feeder ball 14a and the vertical height from the initial point, when the former is defined as a horizontal axis and the latter is defined as a vertical axis.

As shown in FIG. 6, the ascending rail 143a has an upward slope along the guide wall 142a. The inclination of the ascending rail forms a smooth sine curve such that it is small at the beginning, gradually becomes large, and then becomes small again at the end. In contrast, the descending rail 144a is downwardly inclined along the guide wall 142a. The inclination of the descending rail 144a forms a sine curve that gradually becomes larger in the conveyance direction toward the downstream direction, and the amplitude of the sine curve of the descending rail 144a is smaller than that of the ascending rail 143a. This allows the ascending rail 143a to reliably convey the objects in the upward direction and the descending rail 144a to accelerate the conveyed objects in a short time so that they can be aligned.

It is preferable that the inclination of the ascending rail 143a and the descending rail 144a form a sine curve as shown in FIG. 6 so as to facilitate smooth conveyance and alignment of the objects, but they may be a different type of smooth curve or a straight line.

The ascending rail 143a is formed so as to extend to a location that is 180° ahead of the starting point relative to the center of the bottom wall 141a, and the descending rail 144a is formed so as to extend to a location that is 90° ahead of the end of the ascending rail 143a. In the present embodiment, the ascending rail 143a directly connects to the descending rail 144a; however, a conveyance path that is parallel to the horizontal floor may be disposed between the ascending rail 143a and the descending rail 144a.

As shown in FIG. 6, the end of the descending rail 144a (the location 270° from the stating point) has the greatest downward inclination, and the aligning rail 145a and the guide rail 149a are sequentially connected from this location. The inclinations of the aligning rail 145a and the guide rail 149a are formed so as to maintain the sine curve of the descending rail 144a.

The structure of the vibrating feeder 12b is the same as that of the vibrating feeder 12a described above. Accordingly, the objects are aligned and conveyed from the feed portions 146a and 146b of the vibrating feeders 12a and 12b toward the carrying device 20.

As shown in FIGS. 1 and 2, the carrying device 20 is provided with a forward conveying member 21, return conveying members 22a and 22b, and a back/front reversal device 23. The forward conveying member 21 receives the objects from the vibrating feeders 12a and 12b and transports them in two lines (right and left). The return conveying members 22a and 22b are disposed on the right and left of the forward conveying member 21 and linearly convey the objects in the direction opposite to the conveying direction of the forward conveying member 21. The back/front reversal device 23 receives the objects from each line of the forward conveying member 21, turns the objects over and then transfers them to the return conveying members 22a and 22b.

Both the forward conveying member 21 and the return conveying members 22a and 22b are formed from conveyor belts, which are driven at the same speed by a servomotor or the like. Each of the conveying belts is formed of a milky-colored semitransparent material with light transmittance and light diffusibility. For example, a polyester belt provided by Nitta Corporation (product name: New Light Grip P-0) is usable. The conveying belt does not have to be milky-colored. It is preferable that the conveying belt be a light color that can exhibit light transmittance and light diffusibility for reliably inspecting the appearance of the object D as described later. Specifically, the conveying belt has a Munsell value of preferably not less than 7, more preferably not less than 7.5, and even more preferably not less than 8. However, even when the Munsell value of the conveying belt is about 5, reliable appearance inspection can be conducted if the lightness of the object itself is low. The conveying belt may be formed of a transparent material, and the same effects as those of the present embodiment can also be achieved in this case. When a conveying belt formed of a transparent material is used, it is preferable that a bright light source be used as a lower lighting device 32.

In the conveyance plane of each conveying belt, a groove 24 extending in the conveying direction is formed in such a manner that it corresponds to each line of the objects. The groove 24 has a circular cross section (including an elliptic arc) that has a width that is smaller than that of the object, and a depth that can hold only a portion of the object (for example, in the case of tablets, about 0 mm to 1 mm). Press rollers 25 are provided at the location where the conveyed objects are transferred from the vibrating feeder 12a (12b) to the forward conveying member 21, as shown in FIG. 1.

As shown in FIGS. 7 and 8, the back/front reversal device 23 is provided with inclined drums 231a and 231b and an inversion drum 232. The inclined drums 231a and 231b are slidably and rotatably supported relative to the inclined surfaces 233a and 233b, which are disposed on the right and left sides of the suction box 233, which is connected to a vacuum pump (not shown). In this structure, as shown in FIG. 7, when seen along the conveying direction of the forward conveying member 21 and return conveying members 22a and 22b, the rotation axes R1 and R2 are arranged so as to be inclined relative to the conveyance planes of the forward conveying member 21 and return conveying members 22a and 22b (i.e., when the appearance inspection device 1 is placed on a horizontal floor, they are inclined relative to the horizontal surface).

The shapes of the inclined drums 231a and 231b and inversion drum 232 may be disc-like, rather than the usual cylinder-like (drum) shape. In the present embodiment, the inclined drums 231a and 231b have a disc-like shape and the inversion drum 232 has a cylinder-like shape.

In the peripheral surfaces of the inclined drum 231a and 231b, many suction ports 234a and 234b are continuously formed along the circumferential direction. The suction ports 234a and 234b are communicably opened to the inside of the suction box 233 via the notches 235a and 235b in the inclined surfaces 233a and 233b of the suction box 233. This arrangement allows the inclined drums 231a and 231b to hold, by means of suction, each of the objects D conveyed in each line of the forward conveying member 21, and then to transfer them in the direction shown by the arrow in FIG. 8.

The inversion drum 232 is supported in such a manner that its rotation axis extends in the horizontal direction so that the inversion drum 232 rotates by sliding relative to the perpendicular plane 236 of the suction box 233. In both sides of the peripheral surfaces of the inversion drum 232, many suction ports 237a and 237b are continuously formed along the circumferential direction. The suction ports 237a and 237b are communicably opened to the inside of the suction box 233 via the notch 238 formed in the perpendicular plane 236. This arrangement allows the objects D conveyed by the inclined drum 231a and 231b to rotate with inclination and be transferred to the suction ports 237a and 237b of the inversion drum 232 at a location separated therefrom by the distance h in the direction parallel to that the forward conveying member 21 and the return conveying members 22a and 22b are arranged (i.e., perpendicular to the conveying direction along the conveyance plane), and then the conveyed objects D are held by suction on the peripheral surface of the inversion drum 232.

The transfer distance h of the conveyed objects D in the parallel direction corresponds to the distance between the groove 24 of the forward conveying member 21 and the groove 24 of the return conveying members 22a and 22b. The conveyed objects D are guided above the grooves 24 of the return conveying members 22a and 22b by the rotation of the inversion drum 232 in the direction shown by the arrow of FIG. 8, and then transferred to the return conveying members 22a and 22b by injecting compressed air from the compressed air nozzle 239.

As shown in FIGS. 1 and 2, five image-pickup devices 30a, 30b, 30c, 30d, and 30e are disposed in the vicinity of the forward conveying member 21 and the return conveying members 22a and 22b in such a manner that images of the conveyed objects D being conveyed can be captured from upper directions. Lighting devices 31 and 32 are disposed immediately above and below the forward conveying member 21 and the return conveying members 22a and 22b. The lighting devices 31 and 32 illuminate the conveyed objects D by guiding the light emitted from an incandescent lamp or like light source using optical fiber.

All of the image-pickup devices 30a to 30e are line sensor cameras, which scan in the direction intersecting the image-pickup axis and output signals corresponding to the lightness of the conveyed objects D (i.e., output signals substantially proportional to the light amount received by the line sensors). Among the image-pickup devices 30a to 30e, two image-pickup devices 30a and 30b are arranged so that they face each other on the image-pickup axis I1 as seen in a plan view. Two other image-pickup devices 30c and 30d are arranged so that they face each other on the image-pickup axis I2 that perpendicularly intersects the image-pickup axis I1 as seen in a plan view. The image-pickup devices 30a to 30d are arranged so that they can substantially simultaneously capture images of the conveyed objects D being conveyed in two lines by the forward conveying member 21, and, the conveyed objects D being conveyed by return conveying members 22a and 22b in one line from upper oblique directions on the image-pickup axis I1 or I2. In other words, each of the image-pickup devices 30a to 30d can simultaneously capture an image of four conveyed objects D in each conveying line along the same scanning line.

The remaining image-pickup device 30e is disposed so that it can capture images of the conveyed objects D from directly above. In other words, the image-pickup device 30e can capture images of the front surfaces of the conveyed objects D being conveyed by the forward conveying member 21 and the back surfaces of the conveyed objects D being conveyed by the return conveying members 22a and 22b along the same scanning line.

The defect detection device 40 is provided with an image formation member 41 and an image processing member 42. The image formation member 41 generates two-dimensional image data of the conveyed objects D based on the signals output from each of the image-pickup devices 30a to 30e. The image processing member 42 extracts the region in which the amount of light received is less than a predetermined level from the image data generated by the image formation member 41 to conduct inspection. The defect detection device 40 determines whether or not the individual object D passes or fails the inspection based on the inspection results of the image processing member 42. Each of the objects D conveyed by the return conveying members 22a and 22b is classified into "accepted" or "rejected" using the screening device 43. The accepted objects D are transferred onto a defect-free product recovery belt 44 to be picked up. The rejected objects are discharged into a defective product holder 45.

The operation of the appearance inspection device 1 is explained below. In FIGS. 1 and 2, when many objects to be tested, such as tablets, are placed in the hopper 10, the objects are supplied to the vibrating feeders 12a and 12b via the chutes 11a and 11b, and then conveyed along the ascending rail 143a, descending rail 144a, and aligning rails 145a shown in FIG. 3.

Each of the ascending rail 143a, descending rail 144a, and aligning rails 145a has an inclination as shown in FIG. 6. Therefore, the objects are conveyed at a low speed on the ascending rail 143a, which has an upward slope, and they are conveyed at a higher speed on the descending rail 144a, which has a downward slope. Accordingly, the piling of the objects D conveyed on the ascending rail 143a as shown in FIG. 9(a) separates as shown in FIG. 9(b) when they are transferred onto the descending rail 144a and their speed is accelerated. Therefore, while being conveyed on the descending rail 144a, the conveyed objects D are aligned as shown in FIG. 9(c). The descending rail 144a allows the conveyed objects D to align along the guide wall 142a before being supplied to the aligning rails 145a, so that the conveyed objects D can be introduced into the aligning rails 145a smoothly. The aligning rails 145a are structured so that the conveyed objects pass therethrough in a single line.

The conditions of the objects conveyed by a vibrating feeder are explained below with reference to FIG. 10. As shown in FIG. 10(a), in a vibrating feeder whose torsion axis C of the torsional vibration aligns with the vertical direction V, the force F for transporting the object D with the torsional vibration, regardless whether the object is on an ascending rail R1 or on a descending rail R2, is applied in the same direction relative to the horizontal floor. Accordingly, the angle θ1 made between the conveyance plane of the ascending rail R1 and the application direction of the conveyance force F is small, and the angle θ2 made between the convey-ance plane of the descending rail R2 and the application direction of the conveyance force F is large.

In the vibrating feeder 12a of the present embodiment, a torsion axis C of the torsional vibration is inclined relative to the vertical direction V as shown in FIG. 10(b). Therefore, the angle θ3 formed between the conveyance plane of the ascending rail 143a and the application direction of the conveyance force F is larger than the angle θ1 shown in FIG. 10(a), and the angle θ4 formed between the conveyance plane of the descending rail 144a and the application direction of the conveyance force F is smaller than the angle θ2 shown in FIG. 10(a). Accordingly, the vibrating feeder 12a of the present embodiment makes it possible to apply stronger climbing force to the conveyed objects D in the ascending rail 143a, and, in the descending rail 144a, the objects D can be conveyed faster.

As a result, in the vibrating feeder having its torsion axis C aligns with the vertical direction V as shown in FIG. 11(a), the conveyed objects D supplied to the bottom wall R rise on the ascending rail R1 in a piled status (status S1→S2→S3), sufficient acceleration does not take place when they move down the descending rail R2, and they are supplied to the aligning rail R3 in a status (status S4→S5) in which they are not sufficiently spread. This increases the excessive conveyed objects D, which are supplied to the bottom wall R without being aligned in the aligning rail R3 (status S6), and makes it difficult to supply conveyed objects D from the guide rail R4 at a sufficient speed (status S7).

In contrast, with the vibrating feeder 12a of the present embodiment, which has a torsion axis C of torsional vibration inclined relative to the vertical direction V, a large number of conveyed objects D supplied to the bottom wall 141a reliably rise on the ascending rail 143a due to a large climbing force in a piled status (status S1→S2→S3) at a slow speed, and the objects come down the descending rail 144a with sufficiently accelerated speed so that the conveyed objects D can be sufficiently aligned (status S4→S5). Accordingly, there are almost no excessive conveyed objects D supplied from the aligning rail 145a to the bottom wall 141a (status S6). This allows the conveyed objects D to be supplied from the guide rail 149a at high speed. (Status S7).

The vibrating feeder 12a of the present embodiment is structured so that the downward inclination of the descending rail 144a gradually increases in the downstream conveyance direction of the objects D. This allows the conveyed objects D to smoothly increase in speed and to be easily spread.

The descending rail 144a is structured so that its downward inclination becomes the greatest at the portion connecting to the aligning rail 145a, and therefore the conveyed objects D can be supplied to the aligning rail 145a in the most spread condition, and high-speed conveyance of the objects D can be reliably conducted.

By setting the amplitude of the sine curve of the descending rail 144a smaller than that of the ascending rail 143a as in the present embodiment, a step can be easily formed between the aligning rail 145a and the bottom wall 141a, and excessive objects D returning from the aligning rail 145a to the bottom wall 141a can be easily guided to the ascending rail 143a again.

The arrangement of the vibrating feeder 12a of the present invention allows the conveyed objects to be automatically aligned, and therefore a regulation plate for forcibly aligning the objects is unnecessary. Even if a regulation plate is provided, collisions of the conveyed objects and the regulation plate can be prevented and the risk of chipping or cracking of the conveyed objects can be reduced. The greater the difference in speed between the ascending rail and the descending rail, the more remarkable the effects. Therefore, the vibrating feeder of the present invention is particularly effective when high-speed conveyance is performed (for example, 100,000 to 160,000 tablets an hour per line). The inclination angle and connection location of the ascending rail and the descending rail can be suitably selected depending on the conveyance amount and shape of the test objects so that the test objects can be easily aligned.

The aligned objects discharged from the vibrating feeders 12a and 12b are transferred onto the forward conveying member 21. As shown in FIG. 12, by setting the supply speed from the vibrating feeders 12a and 12b as V1, and the conveyance speed of the forward conveying member 21 as V2, which is faster than V1, the space between the conveyed objects D in each line of the forward conveying member 21 can be increased. A desirable space can be obtained by adjusting the difference between V1 and V2. The press rollers 25 rotate at substantially the same speed as the conveyance speed V2 of the forward conveying member 21. This prevents jumping or misalignment of the conveyed objects D when they are transferred from the vibrating feeders 12a and 12b to the forward conveying member 21, and reliably positions the conveyed objects D on the groove 24 of the forward conveying member 21.

As shown in FIG. 13(a), part of the bottom surface of each object D positioned on the groove 24 is placed in the groove 24. Therefore, as shown in FIG. 13(b), the height L1 of the forward conveying member 21 as measured from the conveyance plane becomes slightly shorter than the actual height of the object. When the conveyed objects D horizontally rotate while being conveyed on the forward conveying member 21, the conveyed objects D are stabilized in the position (direction) that makes the height from the conveyance plane of the forward conveying member 21 shorter, as shown in FIGS. 14(a) and 14(b), and are conveyed while maintaining the position in which the height becomes the lowest L2.

By forming grooves 24 in the forward conveying member 21, even if the conveyed objects are irregularly shaped tablets or capsules, they can automatically be adjusted so that their position has maximum stability. This arrangement allows each object to be conveyed in an aligned condition with a fixed position. It is preferable that the groove 24 have a circular (including an elliptic arc) cross section as in the present embodiment. This arrangement allows the height of the conveyed objects from the conveyance plane to easily vary in accordance with their position. However, the cross section of the groove 24 does not have to be an arc and may be rectangular. If the conveyed objects D have a cross section that does not cause a change in the position during the conveyance, such as a square shape, the groove 24 may be omitted.

The conveyed objects D, after having their positions adjusted on the forward conveying member 21, pass through the image-pickup area where image-pickup devices 30a to 30e are disposed. Subsequently, they are turned over by the back/front reversal device 23, and then conveyed in the opposite direction by the return conveying members 22a and 22b. The operation of the back/front reversal device 23 is the same as that explained above, i.e., by passing through the inclined drum 231a and 231b and the inversion drum 232, which can hold the conveyed objects on the peripheral surfaces thereof, the conveyed objects transferred to the return conveying members 22a and 22b can be reliably turned over. By placing the conveyed objects D in the groove 24 of the return conveying members 22a and 22b, the positions of the conveyed objects D conveyed by the return conveying members 22a and 22b can also be automatically adjusted. The conveyance of the objects D in the forward direction by the forward conveying member 21 and in the reverse direction by the return conveying members 22a and 22b can thus be continuously conducted.

In the image-pickup area of each image-pickup device 30a to 30e, the conveyed objects D are irradiated from above and below thereof with light emitted from the lighting devices 31 and 32. Because the conveying belt used in the forward conveying member 21 and return conveying members 22a and 22b of the present embodiment has a high light-transmitting color, such as a milky-colored semitransparent belt with light transmittance and light diffusion, the conveyed objects D can be uniformly illuminated by radiating light from above and below the conveyed objects D. This arrangement also makes the light-transmitting color that serves as the background of the objects D conspicuous, so the objects D are observed as dark portions.

Each of the four image-pickup devices 30a to 30d scans in the direction perpendicular to the image-pickup axes 11, 12 shown in FIG. 2, so that images of the individual objects D being conveyed on the forward conveying member 21 and the return conveying members 22a and 22b can be captured. As a result, images of the top surface of an object D being conveyed on the forward conveying member 21 are captured from four upper oblique directions W, X, Y, and Z, as shown in FIG. 15. Likewise, images of the back surface of an object D being conveyed on the return conveying members 22a and 22b are captured from four upper oblique directions. Accordingly, a single line of scanning conducted by the image-pickup devices 30a to 30d makes it possible to generate output signals having a degree of light that corresponds with the receptive light. By repeatedly scanning while conveying the objects D, the output signals corresponding to the scanning are sequentially transmitted to the defect detection device 40.

In the present embodiment, the forward conveying member 21 and the return conveying members 22a and 22b are disposed in parallel and arranged so that each object is conveyed in such a manner that its top and back surfaces are exposed. Therefore, by simultaneously capturing images of each object conveyed on the forward conveying member 21 and the return conveying members 22a and 22b along the same scanning line using a plurality of image-pickup devices 30a to 30d, the entire appearance of the object can be easily and reliably inspected.

In the defect detection device 40, based on the output signals from each of the image-pickup devices 30a to 30d, image formation member 41 generates two-dimensional image data corresponding to the scanning line. For example, when an arbitrary image-pickup device scans an object D conveyed on the forward conveying member 21 along the scanning line S1 as shown in FIG. 16(a), the image data generated based on the output signals are as shown in FIG. 16(b).

The objects D are generally tablets, capsules, etc. Therefore, depending on the color of the objects D, the difference in the lightness of color between the objects D and the background is very small. This may make it difficult to distinguish the objects D from background. Because the conveying belt used in the present embodiment is formed of a milky-colored semitransparent material with light transmittance and light diffusion, the lightness on the conveyance plane, which becomes the background, is higher than that of the objects D. As a result, as shown in FIG. 16(b), in the image data, the portion corresponding to the object D can be observed as the portion with less lightness (i.e., the amount of light received by the line sensors is smaller) than the background.

As a result, if a chip e1 and/or a projecting strand of hair e2 exists on the scanning line S1 of the object D as shown in FIG. 16(a), these defects can be observed as the regions b1 and b2 with less lightness (i.e., the amount of light received by the line sensors is smaller) than that of the object D as shown in FIG. 16(b). Objects D are inspected in the following manner. The first criteria value T1 is set higher than the lightness (the amount of light received by the line sensor) of the objects D and then the image processing member 42 extracts the image data having a lightness equal to or lower than the first criteria value T1, so that the objects D can be distinguished from the background. The defects of the objects D can be detected by, for example, setting the lightness (the amount of light received by the line sensor) of the second criteria value T2 lower than that of the objects D, and extracting the image data equal to or lower than the second criteria value T2.

With such a defect detection method, defects protruding from the object and defects in the edge portions, which are sometimes overlooked by conventional methods because they assimilate with the conveying belt, can be reliably detected. Furthermore, not only the edge portions and the outside of the images of the object, but also defects that exist inside the object can be reliably detected. For example, as shown in FIG. 16(a), if a foreign substance is adhered to the object D on the scanning line S2, the foreign substance can be recognized as the region b3 having a signal value lower than the signal level of the object D as shown in FIG. 16(c).

In the present embodiment, images of the top and back surfaces of each object D are captured from four upper oblique directions as described above to detect the presence of defects. This makes it possible to conduct an inspection without a dead angle. In particular, when the object is annular (doughnut shaped), it is difficult to capture images of the defects on the inside perimeter of the object by known methods. However, the appearance inspection device of the present embodiment can reliably capture images of such inside perimeters. Combining this with the ability to conduct reliable defect detection of the image data allows the appearance of the object to be reliably inspected.

In the present embodiment, images of each object are captured along the same scanning line by each of the image-pickup devices 30a to 30d while the object is being conveyed on a forward conveying member 21 and the return conveying members 22a and 22b. This makes it possible to inspect the object by capturing images of the top and back surfaces thereof using the same image-pickup devices 30a to 30d. Therefore, unlike inspections using different image-pickup devices for the front surface inspection and the back side inspection, calibration of the cameras and confirmation of the inspection accuracy do not have to be conducted so often, making camera validation easier.

In the present embodiment, in addition to the above-described four image-pickup devices 30a to 30d, an image-pickup device 30e is further provided for capturing images of the top and back surfaces of the object in the perpendicular direction. The defect detection device 40 generates image data in the image processing member 42 based on the output signals from the image-pickup device 30e, and detects defects mainly in printed portions by comparing this image data with a master image.

The forward conveying member 21 and the return conveying members 22a and 22b convey the objects at predetermined intervals and a predetermined speed. This arrangement allows the defect detection device 40 to specify the object that corresponds to the image data containing defects by determining which image-pickup device 30a to 30e captured the signal, based on the image data that was generated in the image formation member 41, and the timing with which the signal was input. When an object containing a defect is conveyed to the screening device 43, the object is discharged into the defective product holder 45.

One embodiment of the present invention is explained above, but the embodiments of the present invention are not limited to this. For example, in the present embodiment, the image-pickup devices 30a to 30d face each other on two perpendicularly intersecting image-pickup axes as seen in a plan view, so that the number of image-pickup devices can be reduced while also reliably eliminating any dead angle in the captured image. However, insofar as no dead angle is formed, various arrangements are possible, and therefore, for example, the image-pickup axes do not necessarily have to intersect at right angles, and the image-pickup devices 30a to 30d do not have to be disposed so as to face each other.

To simplify camera validation, the present embodiment has a structure in which the forward conveying member 21 and return conveying members 22a and 22b are arranged in parallel, and the image-pickup devices 30a to 30d are disposed so that each of them can capture images of the top and back surfaces of the object along the same scanning line. However, the image-pickup devices may be arranged so as to capture the images of the object conveyed by the forward conveying member 21 and the return conveying members 22a and 22b individually. In this case, the forward conveying member 21 and the return conveying members 22a and 22b do not have to be arranged in parallel, and may have an alternate arrangement depending on the space available.

The number of image-pickup devices for capturing images of an object from an upper oblique direction is four in the present embodiment; however, as long as a plurality of image-pickup devices are provided, the same effects as those of the present embodiment can be attained. In order to reliably prevent any dead angle, it is preferable that three or more image-pickup devices be provided. It is also preferable that the plurality of image-pickup devices be disposed along the periphery of the image-pickup area with the same interval between each image-pickup device so that uniform images can be captured.

In the carrying device 20 of the present embodiment, one of the return conveying members 22a and 22b is disposed on either side of the forward conveying member 21; however, it is also possible to dispose a forward conveying member on both sides of the return conveying member. Furthermore, the conveyance lines of the forward conveying member 21 and the return conveying members 22a and 22b in the present embodiment consist of two lines, but may be a single line, or three lines or more.

In the present embodiment, the back/front reversal device 23 is provided with the inclined drums 231a and 231b and the inversion drum 232. By positioning the rotation axes of the inclined drums 231a and 231b, which receive conveyed objects from the forward conveying member 21, in such a way that they are inclined relative to the conveyance planes of the forward conveying member 21 and the return conveying members 22a and 22b, the conveyed objects from the forward conveying member 21 to the return conveying members 22a and 22b can be transferred by moving the objects in a parallel direction relative to which the forward conveying member 21 to the return conveying members 22a and 22b are arranged. The same effect as that of the present embodiment can also be achieved by using an arrangement wherein the drum (first drum) that receives the objects from the forward conveying member 21 is disposed so that its rotation axis extends along the conveyance planes of the forward conveying member 21 and the return conveying members 22a and 22b (i.e., along the horizontal surfaces), and the drum (the second drum), which receives the objects conveyed from the first drum and transfers them to the return conveying members 22a and 22b, is disposed so that its rotation axis is inclined relative to the same manner as described above. Table 1 shows the results. The number of tablets having a bulk volume of 100 ml was 680±6, and that having a bulk volume of 500 ml was 3400±20.

TABLE 1

| | Angle | | | | | | | | | | |
|---|---|---|---|---|---|---|---|---|---|---|---|
| | 0° | 1° | 2° | 3° | 4° | 5° | 6° | 7° | 8° | 9° | 10° |
| Number of Objects Discharged (Experiment A) | 320 | 336 | 357 | 378 | 386 | 408 | 413 | 403 | 298 | 172 | — |
| Evaluation (Experiment A) | — | C | B | A | A | A | A | A | D | D | — |
| Number of Objects Discharged (Experiment A) | 320 | 327 | 351 | 356 | 369 | 384 | 401 | 418 | 430 | 451 | 385 |
| Evaluation (Experiment A) | — | C | B | B | A | A | A | A | A | A | A |
| Overall Evaluation | — | C | B | A | A | A | A | A | C | C | C | conveyance planes. Alternatively, both the above-mentioned first drum and second drum may be arranged so that their rotation axes are inclined relative to the conveyance planes.

When one or both of the first drum and the second drum are formed as an inclined drum as described above, the inclined drum may be arranged in such a way that its rotation axis is inclined relative to the conveying direction as seen from a position above the conveyance planes. In this case, even if the rotation axis is parallel to the conveyance planes, by rotating and conveying the conveyed objects held on the peripheral surface, the conveyed objects can be transferred in the direction perpendicular to the forward conveying member 21 and the return conveying members 22a and 22b. This allows the conveyed objects to be transferred from the forward conveying member 21 to the return conveying members 22a and 22b.

EXAMPLES

In order to define the preferable range a of the angle formed between the vertical direction V and the central line C as shown in FIG. 4, the following experiment was conducted. A plurality of wedge-shaped main body supporting members 18a having different angles were prepared, the angle formed between the vertical direction V and the central line C was defined as a parameter α, and the speed of the aligned conveyed objects was evaluated.

Tablets having a diameter of 7 mm and a thickness of 3 mm were used as conveyed objects, and they were placed in a feeder ball in such an amount that its bulk volume became 100 ml (in Experiment A) and 500 ml (in Experiment B). Subsequently, starting from the point when each conveyed object became fixed in position and the objects were discharged from the feeder ball, the number of conveyed objects was measured for a period of 10 seconds. A "Parts Feeder" (Model No.: DMS-25) manufactured by Shinko Electric Co., Ltd. was used as the vibrating feeder, and the horizontal amplitude and vertical amplitude of the vibrating feeder were set to 0.9 mm and 0.08 mm respectively. The feeder ball that was used had a diameter of 400 mm, and exhibited a curve from the starting point to the height thereof as shown in FIG. 6.

As a Comparative Example, a feeder body 16a was directly placed on a floor surface F without using the main body supporting member 18a (i.e., the angle α of FIG. 4 was 0°), and the number of the conveyed objects was measured in the same manner as described above. Table 1 shows the results. The number of tablets having a bulk volume of 100 ml was 680±6, and that having a bulk volume of 500 ml was 3400±20.

In Table 1, the columns Evaluation (Experiment A) and Evaluation (Experiment B) indicate the increased percentage of discharged objects compared to the discharged objects of the Comparative Example (angle α of 0°). The case where the discharge number decreased was ranked D, the case where the discharge number increased by less than 5% was ranked C, the case where the discharge number increased by 5 to 15% was ranked B, and the case where the discharge number increased by not less than 15% was ranked A. The column Overall Evaluation was ranked C when the ranking combinations of (Experiment A) and (Experiment B) were (C, C), (A, D), or (A, -); B when the ranking combination was (B, B); and A when the ranking combination was (A, B) or (A, A). Regarding Experiment A, the number of discharged objects was not evaluated when the angle α was 10°, but it was confirmed that the objects can be conveyed.

As is clear from the results of Table 1, as the angle α formed between the vertical direction V and the central line C becomes greater, the number of objects discharged increases and the speed of the aligned conveyance also increases. However, if the angle α becomes unduly large, it becomes difficult to sufficiently achieve the conveyance ability of the vibrating feeder, resulting in a decreased number of discharged objects. According to the results, it is preferable that the angle α be in the range of 1° to 10°, more preferably 2° to 7°, and particularly preferably 3° to 7°.

BRIEF DESCRIPTION OF DRAWINGS

FIG. 1 is a side elevation view of an appearance inspection device according to one embodiment of the present invention.

FIG. 2 is a plan view of the main components of the appearance inspection device of FIG. 1.

FIG. 3 is an enlarged plan view of the vibrating feeder of FIG. 1.

FIG. 4 is a side elevation view of the vibrating feeder of FIG. 1.

FIG. 5 is an enlarged view of the principal parts of the vibrating feeder of FIG. 1.

FIG. 6 is a side elevation view of the vibrating feeder of FIG. 3 taken along the chain double-dashed line B.

FIG. 7 shows the rear surface of the back/front reversal device of FIG. 1.

FIG. 8 is an enlarged side view of the back/front reversal device of FIG. 1.

FIGS. 9(*a*) to 9(*c*) illustrate conditions for conveying the object by the vibrating feeder of FIG. 1.

FIGS. 10(*a*) and 10(*b*) are enlarged views of the principal parts illustrating conditions for conveying the objects using the vibrating feeder of FIG. 1, wherein FIG. 10(*a*) shows the conditions of the Comparative Example and FIG. 10(*b*) shows those of the Example.

FIGS. 11(*a*) and 11(*b*) are plan views of the principal parts illustrating conditions for conveying the objects using the vibrating feeder of FIG. 1, wherein FIG. 11(*a*) shows the conditions of the Comparative Example and FIG. 11(*b*) shows those of the Example.

FIG. 12 is an enlarged side view showing the area around the press rollers of FIG. 1.

FIGS. 13(*a*) and 13(*b*) are enlarged views of the principal parts of the forward conveying member illustrating conditions for conveying the objects by the forward conveying member of FIG. 1, wherein FIG. 13(*a*) is a plan view and FIG. 13(*b*) is a side elevation view.

FIGS. 14(*a*) and 14(*b*) are enlarged views of the principal parts of the forward conveying member illustrating other conditions for conveying the objects by the forward conveying member of FIG. 1, wherein FIG. 14(*a*) is a plan view and FIG. 14(*b*) is a side elevation view.

FIG. 15 shows the image-pickup direction as seen in a plan view of the image-pickup device of FIG. 1.

FIGS. 16(*a*) to 16(*c*) illustrate the method for detecting defects based on the image data of the image-pickup device of FIG. 1.

EXPLANATION OF REFERENCE NUMERALS

1 inspection device
10 hopper
12*a*, 12*b* vibrating feeder
14*a* feeder ball
141*a* bottom wall
142*a* guide wall
143*a* ascending rail
144*a* descending rail
145*a* aligning rail
149*a* guide rail
16*a* feeder body
18*a* main body supporting member
20 carrying device
21 forward conveying member
22*a*, 22*b* return conveying member
23 back/front reversal device
231*a*, 231*b* inclined drum
234*a*, 234*b* suction port
232 inversion drum
237*a*, 237*b* suction port
24 groove
25 press rollers
30*a* to 30*e* image-pickup devices
31, 32 lighting devices
40 defect detection device
41 image formation member
42 image processing member
D conveyed objects
V vertical direction
C central line (torsion axis)
F floor surface

The invention claimed is:

1. A vibrating feeder comprising:

a feeder ball having a circular bottom wall and a conveyance path formed along the periphery of the bottom wall;

a feeder body for supporting the feeder ball so as to apply torsional vibration and for conveying objects supplied to the bottom wall along the conveyance path; and a main body supporting member for supporting the feeder body;

the conveyance path comprising an ascending rail and a descending rail that is disposed downstream from the ascending rail in the conveyance direction;

the main body supporting member supporting the feeder body on a horizontal floor so that a torsion axis, which is the center of the torsional vibration, is inclined relative to the vertical direction; and the ascending rail and the descending rail respectively conveying the objects upwardly or downwardly relative to the horizontal direction with the feeder body being supported by the horizontal floor via the main body supporting member.

2. The vibrating feeder according to claim 1, wherein the descending rail is structured so that its inclination gradually becomes larger toward the downstream in the conveyance direction of the objects.

3. The vibrating feeder according to claim 1, wherein the conveyance path comprises an aligning rail for aligning the objects by narrowing the width of the conveyance path toward the downstream in the conveyance direction in the descending rail; and the descending rail is structured so that the downward inclination is the greatest at the portion where the descending rail is connected to the aligning rail.

4. The vibrating feeder according to claim 1, wherein the ascending rail and the descending rail have inclinations of sine curves when developed linearly along the conveyance direction and seen from the side; and the amplitude of the sine curve of the descending rail is smaller than that of the sine curve of the ascending rail.

5. The vibrating feeder according to claim 1, wherein the descending tail is downwardly inclined toward the outer radial direction.

6. The vibrating feeder according to claim 1, wherein the angle between the vertical direction and the torsion axis is 3° to 7°.

7. The vibrating feeder according to claim 1, wherein the angle between the vertical direction and the torsion axis is 2° to 7°.

8. The vibrating feeder according to claim 1, wherein the angle between the vertical direction and the torsion axis is 1° to 10°.

9. A carrying device provided with the vibrating feeder of claim 1 for use in conveying objects, comprising:

a conveying means for receiving the objects delivered by the vibrating feeder and conveying the objects in a single direction; and press rollers for pressing the objects against the conveyance plane of the conveying means disposed in a location where the objects are transferred from the vibrating feeder to the conveying means.

10. An appearance inspection device provided with the vibrating feeder of claim 1 for inspecting the appearance of the objects, comprising:

a forward conveying means for receiving the objects delivered by the vibrating feeder of claim 1 and conveying the objects in a single direction;

a returning means for conveying the objects in the direction opposite to that of the forward conveying means, the returning means being disposed in parallel to the forward conveying means;

a back/front reversal means for turning over the front and back surfaces of the objects delivered by the forward conveying means and supplying the objects to the returning means;

a plurality of image-pickup means for capturing images of each object being conveyed by the forward conveying means and returning means from upper oblique directions; and a defect detection means for detecting the presence of defects based on image data captured by the image-pickup means.

* * * * *